(12) United States Patent
McNulty et al.

(10) Patent No.: US 11,185,313 B2
(45) Date of Patent: Nov. 30, 2021

(54) TOILET BAG FOR COLLECTING BODILY WASTE

(71) Applicant: Region Hovedstadens Apotek, Herlev (DK)

(72) Inventors: Helle Ølgaard McNulty, Hellerup (DK); Paul McNulty, Copenhagen K (DK)

(73) Assignee: Region Hovedstadens Apotek, Herlev (DK)

( * ) Notice: Subject to any disclaimer, the term of this patent is extended or adjusted under 35 U.S.C. 154(b) by 76 days.

(21) Appl. No.: 16/605,592

(22) PCT Filed: Mar. 23, 2018

(86) PCT No.: PCT/EP2018/057467
§ 371 (c)(1),
(2) Date: Oct. 16, 2019

(87) PCT Pub. No.: WO2018/192742
PCT Pub. Date: Oct. 25, 2018

(65) Prior Publication Data
US 2020/0129161 A1    Apr. 30, 2020

(30) Foreign Application Priority Data

Apr. 20, 2017   (EP) ..................... 17167263

(51) Int. Cl.
*A61B 10/00* (2006.01)
*A47K 11/02* (2006.01)
*A47K 11/10* (2006.01)

(52) U.S. Cl.
CPC ........ *A61B 10/0038* (2013.01); *A47K 11/026* (2013.01); *A47K 11/105* (2013.01); *A61B 10/007* (2013.01)

(58) Field of Classification Search
CPC .................................................. A61B 10/0038
USPC ..................................................... 4/484, 479
See application file for complete search history.

(56) References Cited

U.S. PATENT DOCUMENTS

| | | |
|---|---|---|
| 4,882,794 A | 11/1989 | Stewart, III |
| 7,073,212 B1 | 7/2006 | Moffat |
| 2001/0034904 A1 | 11/2001 | Phillips et al. |
| 2006/0090253 A1 | 5/2006 | El Haje |
| 2007/0260204 A1 | 11/2007 | Akagi et al. |
| 2010/0175178 A1 | 7/2010 | Mrugala |
| 2013/0123562 A1 | 5/2013 | Mullowney et al. |
| 2016/0045086 A1 | 2/2016 | Arroyo |

FOREIGN PATENT DOCUMENTS

| | | |
|---|---|---|
| CN | 102026572 A | 4/2011 |
| CN | 202355331 U | 8/2012 |
| WO | 2007/076593 A1 | 7/2007 |

OTHER PUBLICATIONS http://www.cleanis.com/carebag/carebagtoilet-bowl-liner-with-super-absorbent-pad/.

*Primary Examiner* — Lori L Baker
(74) *Attorney, Agent, or Firm* — Dinsmore & Shohl LLP

(57) ABSTRACT

A device for conveniently collecting bodily waste from patients. One embodiment relates to a disposable bag comprising a plastic bag attachable to a toilet, the bag being fabricated from a material suitable for collecting bodily waste, such as urine, feces and vomit, which contains toxic materials from chemotherapy treatment, and a hem defining an opening of the bag with an elastic band located inside the hem configured for securing the bag to the toilet during use.

27 Claims, 6 Drawing Sheets

STEP 1

Put on disposible gloves

STEP 2

Attach bag 1 to cover the toilet bowl and seat

STEP 3

After use close bag 1 and place in yellow bag 2

STEP 4

Zip the yellow bag 2 and place in waste system

TOILET BAG FOR COLLECTING BODILY WASTE

REFERENCE TO RELATED APPLICATIONS

This application is a U.S. national stage application of PCT/EP2018/057467, filed Mar. 23, 2018, which claims priority from European Patent Application No. EP1716263.7, filed Apr. 20, 2017, the entire content of both of which is incorporated herein by reference.

FIELD OF THE INVENTION

The present disclosure relates to a device for conveniently collecting bodily waste from patients, in particular to prevent certain bodily waste from ending up in nature.

BACKGROUND OF THE INVENTION

Patients receiving chemotherapy for treating cancer may be treated at home or may be sent home shortly after ambulatory treatment. Drugs used for chemotherapy treatment are highly toxic, as they are generally both carcinogenic, genotoxic and mutagenic. During preparation great care is taken not to expose the staff to the drugs by using specially designed preparation rooms and various protective clothes and nurses are also appropriately protected during administration of medication to the patient. Patients in chemotherapy will of course be exposed to the drugs during treatment, but after the drugs have been administered to the patients all precautions seem to be forgotten. In reality the patients excrete drugs or metabolites after chemotherapy treatment in urine and feces for about 3-5 days after each treatment cycle. When patients are at home, this waste is going into the normal sewage system. The different substances, in Denmark more than 70, are very difficult to remove with normal sewage treatment methods. Therefore, this waste requires special treatment to prevent it from ending up in nature and the general environment.

SUMMARY OF THE INVENTION

A purpose of the present disclosure is to avoid that drugs excreted from patients treated with chemotherapy end up in nature. This will reduce the negative environmental impact from chemotherapy drugs currently being discharged into the environment through the sewage system. Another purpose of the present disclosure is to protect the patient and people around the patient, such as family members, from being exposed to the toxic materials in chemotherapy drugs.

Collecting bodily waste from patients in chemotherapy in an easy, safe and convenient fashion is achieved by the presently disclosed disclosure comprising a disposable plastic bag attachable to a toilet, the bag being fabricated from a material suitable for collecting bodily waste, such as urine, feces and vomit, which contains toxic materials from chemotherapy treatment. The preferred embodiment of the bag comprises a hem defining an opening of the bag, preferably with an elastic band, or similar, located inside the hem configured for securing the bag to the toilet during use.

The toxic drugs used for chemotherapy treatment are handled with great care when administered by staff members in a hospital setting. It is also advised that any kind of spillage is cleaned in a cautious and thorough manner. This signals that these materials are very harmful and should be kept from entering nature and damage the environment. Today more than 70 different chemotherapy agents are used for cancer treatment and 100,000 doses were used in 2016 in the Capital Region of Denmark alone. By motivating patients to collect urine and feces and dispose the waste via an appropriate clinical waste system, these pollutants can be removed safely and hence reduce the damage to the environment. It is intended that the waste is disposed of via a system for clinical risk waste.

Safety is of very high importance when handling chemotherapy drugs. This is seen at hospitals, where health-care staff prepares chemo drugs in sterile rooms with negative pressure to ensure that the air in the room together with any drug residues does not escape. The staff uses full protective suits, double gloves and masks when preparing the drugs and nurses use protective coats and gloves when administering the iv-drip to patients. Furthermore, it is common practice that caregivers who are pregnant should not give infusion of chemotherapy to patients. Chemotherapy is even being prepared using robots in some hospitals. This eliminates human error and risk of spillage, thereby lowering the risk of treating patients using the wrong drugs and lowering the risk of exposing health-care staff to the toxic materials. These are all clear signals that these dangerous drugs should be handled with the greatest care.

A study was conducted to measure the urinary excretion of chemotherapy drugs in a 48 h period after administering the drug to the patient (J Oncol Pharm Pract. 2013 September; 19(3):208-17). The urine of family members was also tested for 48 h to evaluate exposure of family members to the chemotherapy drugs. The results showed that the drugs were detected in all samples. Additionally, the drugs were detected at levels of 0.03-7.34 $ng/cm^2$ in wipe samples obtained from the homes of the patients. When conducting wipe tests in preparation rooms for chemotherapy drugs, a concentration of 25 $pg/cm^2$ is cause for concern, corresponding to 0.025 $ng/cm^2$. This means that the wipe test from the homes of the patients show concentrations higher than what is accepted when preparing the drugs. Chemotherapy patients treated at their home or being sent home shortly after treatment is therefore associated with a risk of exposing relatives to the same toxic and dangerous chemotherapy drugs being administered to the patient. This stresses the importance and necessity of collecting waste containing chemotherapy drugs such that the exposure to the patient and relatives is lowered as much as possible.

Another purpose of the disclosure is to provide a disposable bag suited for containing bodily waste with toxic materials from patients in chemotherapy, which is simultaneously easy and convenient to use. A higher degree of convenience makes it more probable that patients will use the disposable bag, which benefits the environment when disposed of using an appropriate waste system. Another advantage of the disclosure is that it prevents other family members from being exposed to residue from the chemotherapy treatment when using the same toilet as the patient. People are advised to wear gloves when cleaning or handling areas or objects exposed to spill or splash from bodily liquids of the patient and to wash their hands thoroughly with soap afterwards. When using the present disclosure, the toilet is covered and protected from bodily waste such that no spillage should be taken care of afterwards.

The presently disclosed disposable bag provides an easy and convenient way of handling the toxic bodily waste from patients receiving chemotherapy treatment. The bag is fabricated from materials that are capable of containing and retaining the toxic waste from patients in chemotherapy treatment. The bag is furthermore designed to cover the toilet bowl and the toilet seat such that all the waste is safely collected in the bag. This is very hygienic, as all surfaces are protected, and consequently the risk of exposing other family members to the toxic materials is significantly reduced. Other products cover the toilet under the toilet seat and thereby expose the toilet seat to the toxic materials where they can be exposed to others if not cleaned properly.

The elastic band at the edge of the bag of the present disclosure means that the bag is safely attached to the toilet during use. In a preferred embodiment the bag goes through the toilet seat and then folds over and around the seat, thereby covering the toilet seat as well and being kept in place by the elastic band. In another embodiment the bag folds around the edge of the toilet bowl and, again, the elastic band keeps the bag in place. In yet another embodiment, the bag is fabricated form an elastic plastic material and provided with adhesive pads on the outer surface of the bag for securing the bag to the toilet, such as the toilet seat. The adhesive pads may be an alternative to the elastic band for securing the bag to the toilet. A tie cord can be an alternative to the elastic band.

The present disclosure further relates to a kit comprising the disposable bag described above and a second outer bag to put the first bag in after use in case the first bag touched the inside of the toilet bowl and/or for creating an extra seal preventing unpleasant odor from being released from the waste. This second outer bag will furthermore reduce the risk of releasing the waste from the bag in case a hole or tear is formed in one of the bags. In a preferred embodiment the kit further comprises a set of plastic or rubber gloves for extra protection of the person handling the waste.

The presently disclosed bag may furthermore be advantageous if used for collecting waste from patients treated with other types of medication than chemotherapy drugs. The disposable bag may for example also be used to collect waste from patients treated with any type of antibiotics, or for collecting waste from patients having received a radio-contrast agent, which is typically used for imaging the patient using computed tomography, projectional radiography or fluoroscopy.

BRIEF DESCRIPTION OF THE DRAWINGS

In the following the disclosure is described in more detail with reference to the accompanying drawings, in which.

DETAILED DESCRIPTION OF THE INVENTION

Figure 1:
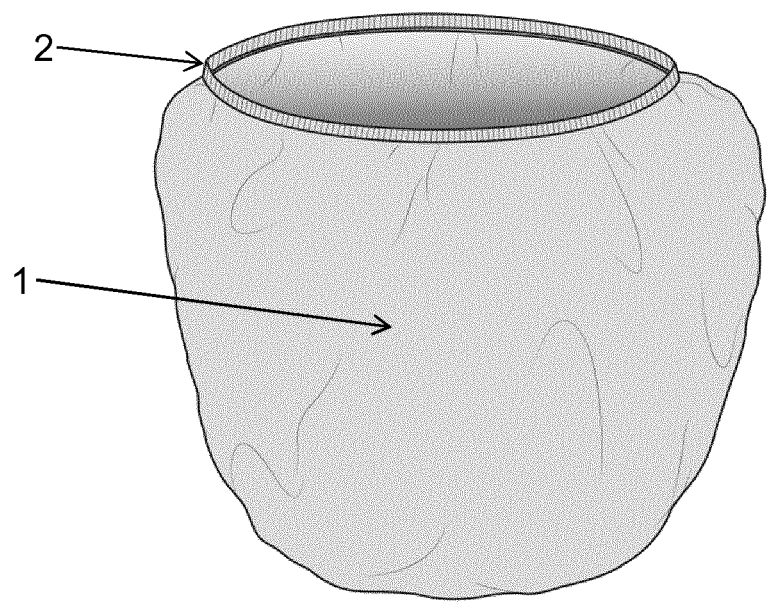
FIG. 1 is a side view of one embodiment of the bag with the opening at the top and the hem at the edge. In this embodiment the elastic band in the hem is in a relaxed configuration.

As mentioned previously, the bag is preferably constructed such that it has a hem at the edge of the bag with an elastic band inside with the purpose of securing the bag to the toilet. In one embodiment the disclosure further comprises a second hem at the edge of the bag containing a string configured for securely closing and/or sealing the bag after use. In a preferred embodiment, the bag contains a string inside the same hem as the elastic band for closing and/or sealing the bag. In yet another embodiment, the elastic band may be withdrawn through an aperture in the hem and used to securely close and/or seal the bag after use.

The bag is intended to be used for a variety of bodily waste, such as urine, feces and vomit. This kind of waste may at least partially consist of liquids. Therefore, in another embodiment of the disclosure, the bag further comprises an absorbent pad inside the bag configured for absorbing liquids from the bodily waste. The liquids are thereby absorbed by the pad and the risk of spillage when closing the bag and subsequent handling of the waste is greatly reduced. In a preferred embodiment of the disclosure, the absorbent pad is attached to the bag using waterproof adhesive. Preferably, the absorbent pad is located at the bottom of the bag such that liquids are guided towards and absorbed by the pad during use. Preferably the absorbent pad contains a super-absorbent polymer or an absorbent gel material, powder, pellets and/or granulate for absorbing the liquids in the waste. This may be a similar material as used in diapers for absorbing liquids. In one embodiment of the disclosure the absorbent pad is configured to absorb at least 300 mL of liquid, more preferably at least 500 mL of liquid, even more preferably at least 750 mL of liquid. Absorbing is preferably understood as once an amount of liquid is absorbed in the pad, no spillage is provided from the absorbent pad during subsequent handling.

The absorbent pad may be configured as a gel and/or for forming a gel when absorbing liquid in the disposable bag. Thereby, any toxic or hazardous materials contained in the liquid are secured in the gel such that is will not leak from the bag during subsequent handling and disposal of the bag. By securing or trapping the toxic materials from the subject in a gel, the risk of spilling the toxic materials and thereby exposing the subject itself and/or other people, such as other family members, is reduced. The absorbent pad may enclose the absorbent material in a water-dissolvable and/or water-permeable material, such as a water soluble polymer, plastic or paper material. Thereby, the absorbent material is released when the bag comes in contact with water and absorbs the liquid. The absorbent material in the pad may be one or more of; sodium polyacrylate (also known as waterlock), poly-acrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

The bag is preferably shaped such that it fits the toilet in the best way possible. The bag may be fabricated from two hemispherical sheets of plastic material joined at the curved edge and with the opening at the straight edge. It is believed that this shape can generally be used with many different kinds of toilets. According to one embodiment a good fit for the toilet may be provided when the bag is configured for being fitted through the toilet seat, folded around the toilet seat and tucked under the toilet seat. In another embodiment the bag is configured for being fitted outside the toilet bowl such that the toilet seat is on top of the bag when in use. Preferably the bag should not touch the inside of the toilet bowl or the water in the toilet during use, as this would lower the sanitation of the disclosure. Therefore, in the preferred embodiment of the disclosure, the bag is configured to conform to the shape of the toilet in a way such that the bag does not touch the inside of the toilet bowl or the water in the toilet. The conformity may be ensured by adjusting the size and shape of the bag. In a further embodiment, the conformity may be ensured by tightening the elastic band such that a sufficient amount of the bag is pulled under the toilet seat which prevents the bag from touching the inside of the toilet bowl or the water in the toilet. In one embodiment of the disclosure the diameter of the opening of the bag in a fully stretched configuration is 40-50 cm, or 50-60 cm, or 60-70 cm, or 70-80 cm, or 80-90 cm. This may also be expressed as the circumference of the opening of the bag, which in another embodiment is 130-135 cm, or 135-140 cm, or 140-145 cm or 145-150 cm. In yet another embodiment the distance from the hem of the bag to the bottom of the bag is 20-25 cm, or 25-30 cm, or 30-35 cm, or 35-40 cm, or 40-45 cm. This distance should preferably be chosen such that the bottom of the bag does not touch the inside of the toilet bowl or the water in the toilet.

In one embodiment the bag is made from a circular sheet of plastic material with a hem along the edge with a string and/or elastic band inside such that it may be attached to the toilet. In another embodiment the bag is substantially semicircular with the opening at the straight edge. This embodiment could comprise two pieces of semicircular sheets of plastic material joined at the curved edge and with the straight edge open. Alternatively, the bag could be substantially square, rectangular, or triangular for a simpler construction. In yet another embodiment of the present disclosure, the bag is shaped like a funnel or a Y such that it is narrower at the bottom of the bag than at the opening at the top. This shape may be achieved by fabricating the bag from two sheets of plastic material that is wide at the top part and narrower at the bottom part and joined at the bottom and side edges. This shape allows the top part of the bag to fit around the toilet seat, while the narrower lower part will gather the waste without extending deep into the toilet bowl, thereby preventing the bag from touching the water in the toilet bowl. The narrower bottom part may also conform better to the toilet which will typically also be narrower at the bottom than at the top there the bag is attached. This shape of the bag may thereby conform better to the toilet than other shapes. As an example, the width of the bag at the bottom may be at least 20 percent, or at least 40 percent, or at least 60 percent smaller than the width of the bag at the opening. Preferably the bottom of the bag when being secured to a toilet and being used extends less than 25 cm below the toilet seat, more preferably less than 20 cm below the toilet seat, even more preferably less than 15 cm below the toilet seat.

The presently disclosed disclosure may in another embodiment be part of a kit comprising the disposable bag for collecting bodily waste and a second outer bag to put the first bag in after use in case the first bag touched the inside of the toilet bowl and/or for creating an extra seal for the waste. The second bag is preferably disposable, such that both bags may be disposed after use. The second bag reduces the risk of leakage from the bag in case one seal malfunctions or a hole/tear forms in one of the bags. Furthermore, the extra seal prevents unpleasant odor from being released from the waste. In some embodiments the bag may further have an added pleasant odor to reduce discomfort when handling the waste. In a further embodiment the kit further comprises a set of plastic or rubber gloves for additional sanitary protection when handling the waste. In one embodiment the second bag is provided with a strip of rigid material at the open end, such as a plastic strip. After the disposable bag with waste is put into the second bag, the strip is folded multiple times to create a seal at the open end of the second bag. Furthermore, the second bag may have an adhesive strip for securing the strip of rigid material to after folding the bag around it.

Another aspect of the disclosure is that the disposable bag is fabricated such that it will safely contain the substances found in the bodily waste from patients receiving chemotherapy treatment. This may be achieved by fabricating the bag from linear low-density polyethylene or polyurethane. The plastic material for the bag may also be a bio-based plastic. Thereby the plastic can be biodegradable and environmentally friendly. Such a bio-based plastic can be one or more of Starch-based plastics, cellulose-based plastics, protein-based plastics, aliphatic polyesters, polyamide 11, bio-derived polyethylene, polyhydroxyurethanes and lipid-derived polymers.

Preferably the material for the bag is puncture-resistant and/or tear-resistant. This may be achieved by fabricating the bag from a plastic material with a thickness of at least 20 microns, more preferably at least 40 microns, yet more preferably at least 60 microns, even more preferably at least 100 microns, most preferably at least 150 microns. In one example of the disclosure, the bag is made from 50 micron thick polyurethane. Puncture-resistance and/or tear-resistance may also be provided by fabricating the bag from multiple layers of for example plastic. Alternatively the bag may be fabricated from an elastic material such as rubber. In one embodiment of the disclosure the bag is made from double layered plastic. Multiple layers add even more safety to the disclosure, as the bag is redundant such that a tear in one layer of the bag does not lead to spillage.

The second bag to put the first bag in after use may also be made from various materials. The second bag may be made from linear low-density polyethylene, or polyurethane, or a bio-based plastic. Biodegradable bio-based plastic is environmentally friendly and may be one or more of Starch-based plastics, cellulose-based plastics, protein-based plastics, aliphatic polyesters, polyamide 11, bio-derived polyethylene, polyhydroxyurethanes and lipid-derived polymers.

The material for the second bag is also preferably puncture-resistant and/or tear-resistant. Again this may be established through the thickness and/or the elasticity of the material, and the second bag may additionally be fabricated from multiple layers of for example plastic. Alternatively the second bag could also be fabricated from an elastic material such as rubber. In one embodiment of the disclosure the second bag is made from double layered plastic. In another embodiment the thickness of the material for the plastic bag is at least 20 microns, more preferably at least 40 microns, yet more preferably at least 60 microns, even more preferably at least 100 microns, most preferably at least 150 microns.

FIG. 1 is a side view of one embodiment of the disposable bag 1 with the elastic band in a relaxed configuration. This embodiment shows a single hem 2 at the edge of the bag containing the elastic band and a string for closing/sealing the bag after use. In a different embodiment the bag may have another hem at the edge such that the elastic band and the string are in separate hems. Alternatively, the bag only has an elastic band which may also be used to close/seal the bag after use.

Figure 2:
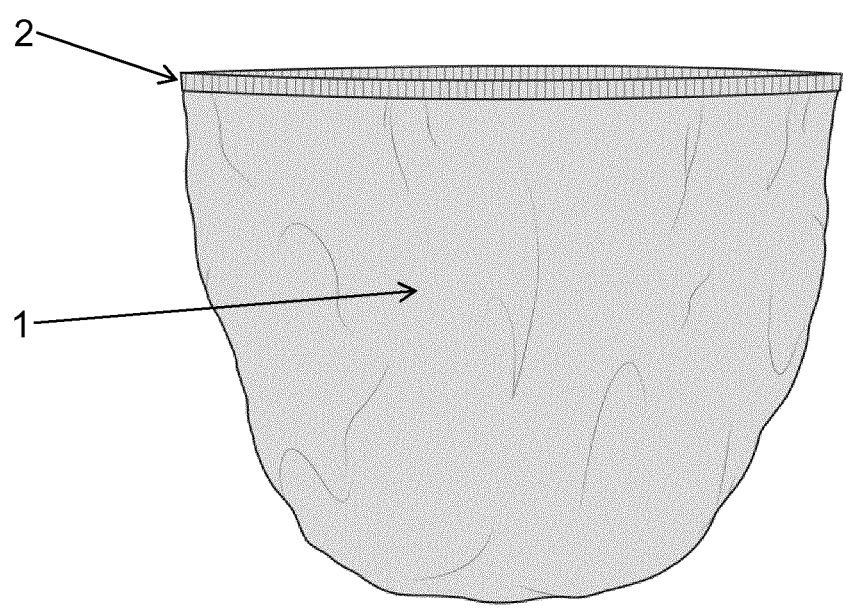
FIG. 2 is a side view of the bag in FIG. 1 where the elastic band in the hem is in a stretched configuration.

FIG. 2 is another side view of the bag 1 in FIG. 1 with the elastic band in a stretched configuration. The bag should be large enough to fit over the toilet seat and be tucked under the seat.

Figure 3:
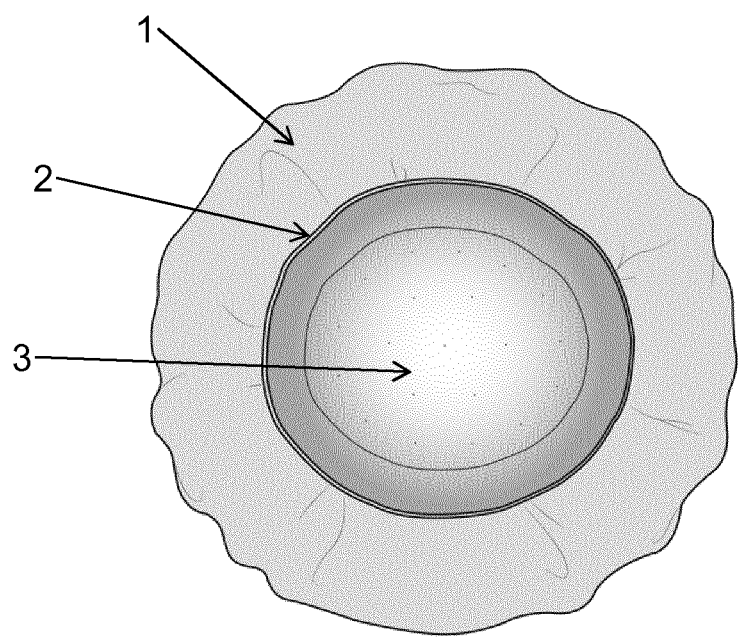
FIG. 3 is a top view of the bag in FIG. 1 with an attached absorbent pad or gel material inside.

FIG. 3 is a top view of the bag 1 in FIG. 1 with an absorbent pad 3 attached to the bottom of the bag. The absorbent pad absorbs liquid from the waste, thereby reducing the risk of spillage when subsequently handling the bag.

Figure 4:
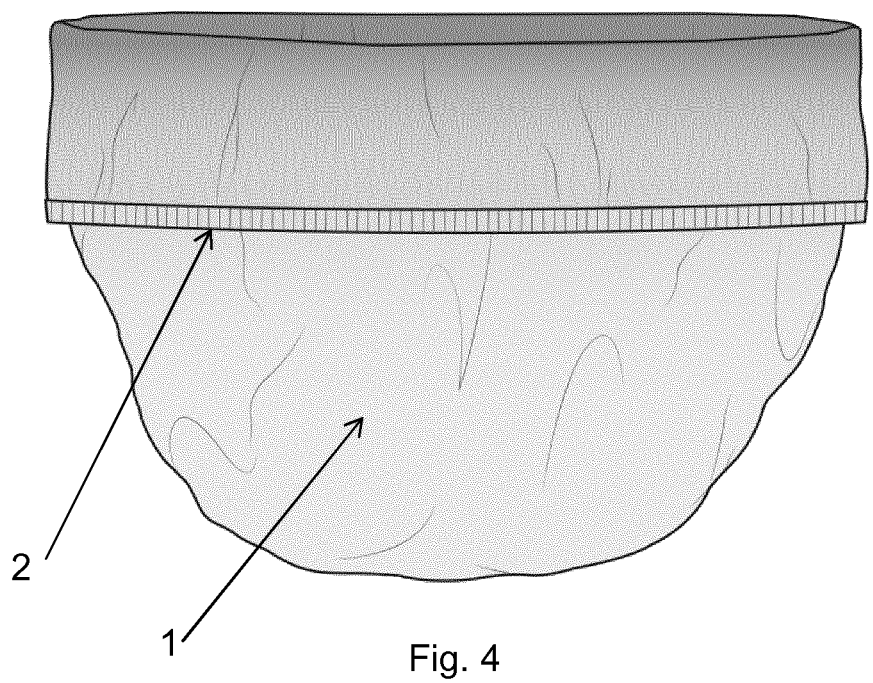
FIG. 4 is a side view of the bag in FIG. 1 where the elastic band in the hem is in a stretched configuration and the edge is folded downwards as it would be when used on a toilet.

FIG. 4 is a side view of the bag in FIG. 1 with the elastic band in a stretched configuration and the edge folded downwards as it would be when used on a toilet. The edge should stretch over the toilet seat and be tucked under the seat, thereby covering the toilet seat completely.

Figure 5:
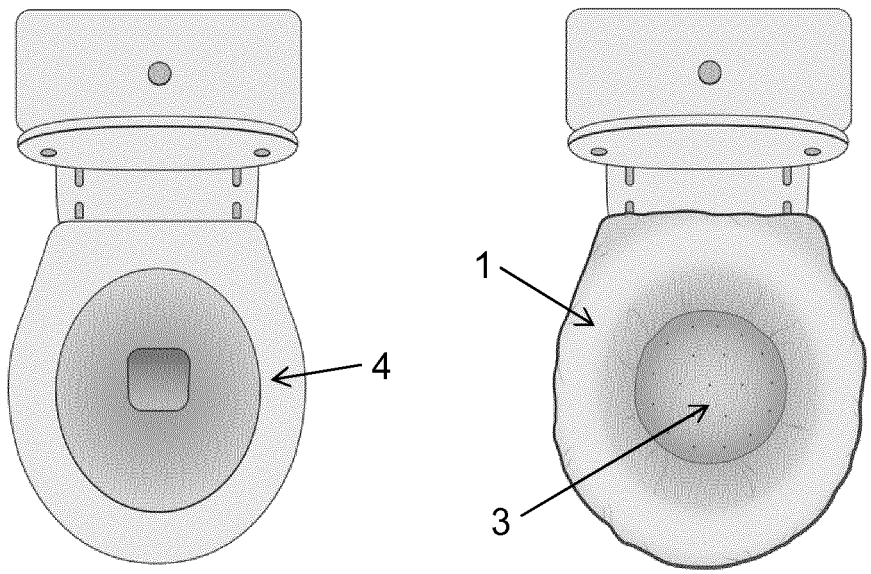
FIG. 5 is a schematic illustration of how the bag in FIG. 1 is attached to a toilet. The left part is a toilet without the bag and the right part is a toilet with the bag attached such that it wraps around the toilet seat.

FIG. 5 is a schematic illustration of how the bag in FIG. 1 is attached to a toilet prior to use. The left part of the figure shows a toilet without the bag and the toilet seat 4 down. The right part shows the toilet with the bag attached to the toilet. The figure shows the preferred embodiment, where the bag is on top of the toilet seat, folds around the seat and is tucked underneath the seat for optimum hygiene.

Figure 6:
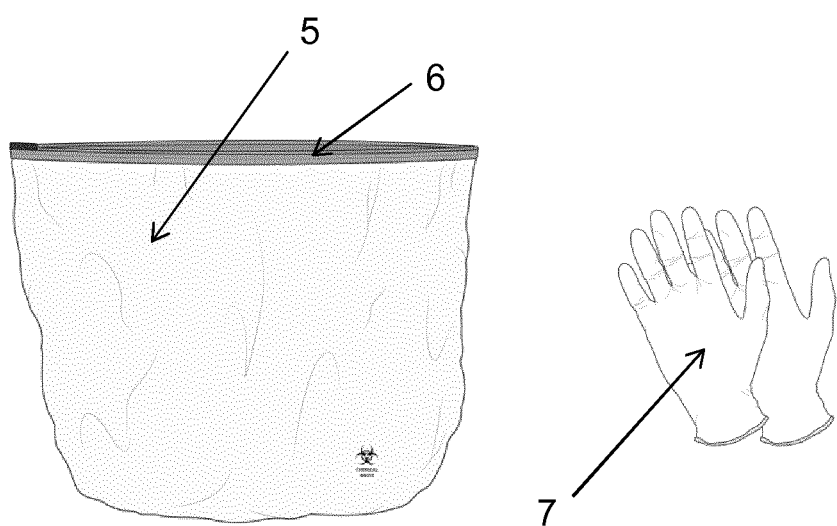
FIG. 6 is a schematic of another embodiment where the bag in FIG. 1 (not shown) is part of a kit further comprising a second outer plastic bag to put the first bag in after use and a set of gloves for handling the waste.

FIG. 6 is a schematic of one embodiment of the items that, combined with the bag in FIG. 1, forms a kit for collecting bodily waste. In this embodiment, a second bag 5 is used to put the first bag in after use and a Ziploc mechanism 6 seals the second bag. A set of rubber/plastic gloves 7 are included for reducing the risk of exposing the skin to the toxic waste when handling the bag after use.

Figure 7:
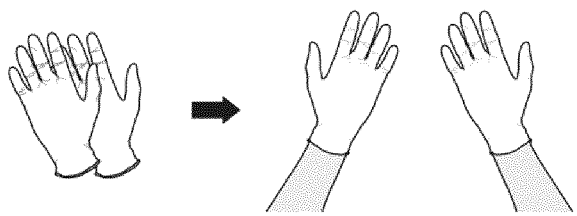
FIG. 7 is a user guide for the kit in FIG. 6 including the bag in FIG. 1.
Figure 7:
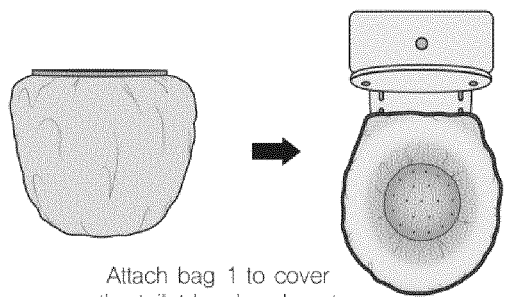
Figure 7:
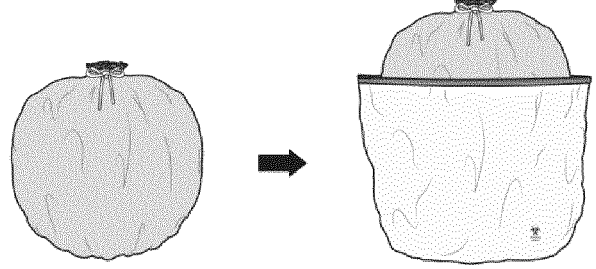
Figure 7:
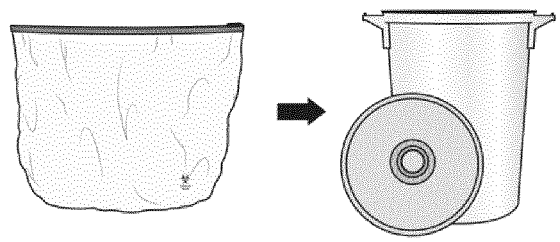

FIG. 7 is a user guide that shows the user how to use the bag and kit. Step 1: put on the rubber/plastic gloves. Step 2: Attach the disposable bag to the toilet, making sure that it is tucked under the toilet seat. Step 3: After use, close the disposable bag and place it in the second bag of the kit. Step 4: Take off the rubber/plastic gloves and place them in the second bag. Close the second bag using the Ziploc mechanism and place the bag in a clinical risk waste disposal system.

Figure 8:
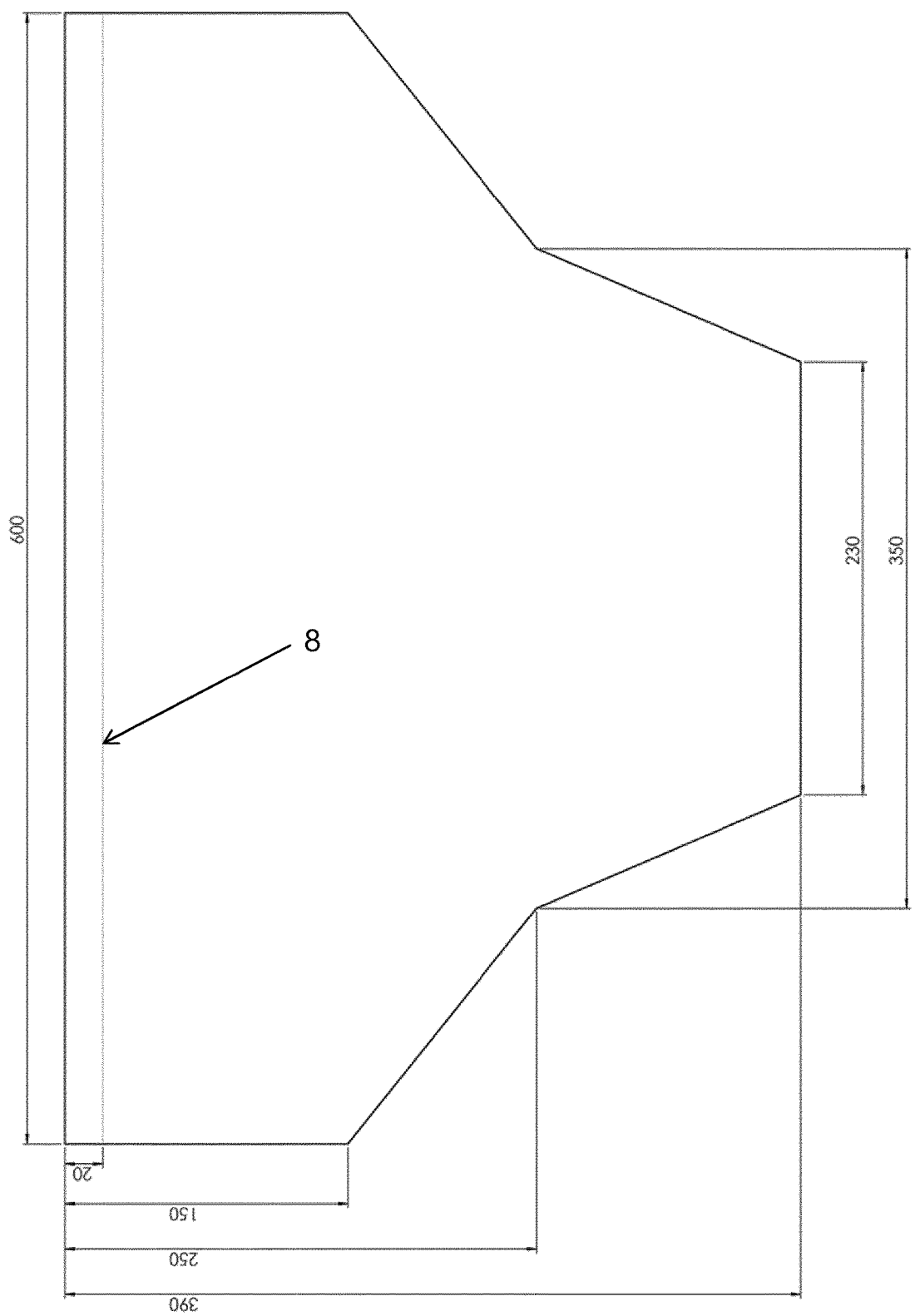
FIG. 8 is a schematic of one embodiment of the bag. This bag is shaped such that it fits the most common types and sizes of toilets around the world.

FIG. 8 is a schematic of one embodiment of the presently disclosed disposable bag. This bag is shaped such that it fits the most common types and sizes of toilets around the world. The bag is in the shape of a funnel or has a Y-shape such that it is narrower at the bottom than at the opening at the top. This may in some embodiments make the bag conform better to the toilet and make it less likely that the bag will touch the inside of the toilet bowl. The measurements indicated in the drawing are an example of the dimensions of the bag, which can vary depending on the application and type of toilet it should be attached to. The open end of the bag may be provided with a hem 8 for a string and/or an elastic band. The hem may be formed by folding the edge of the bag and attach it to the bag itself.

Figure 9:
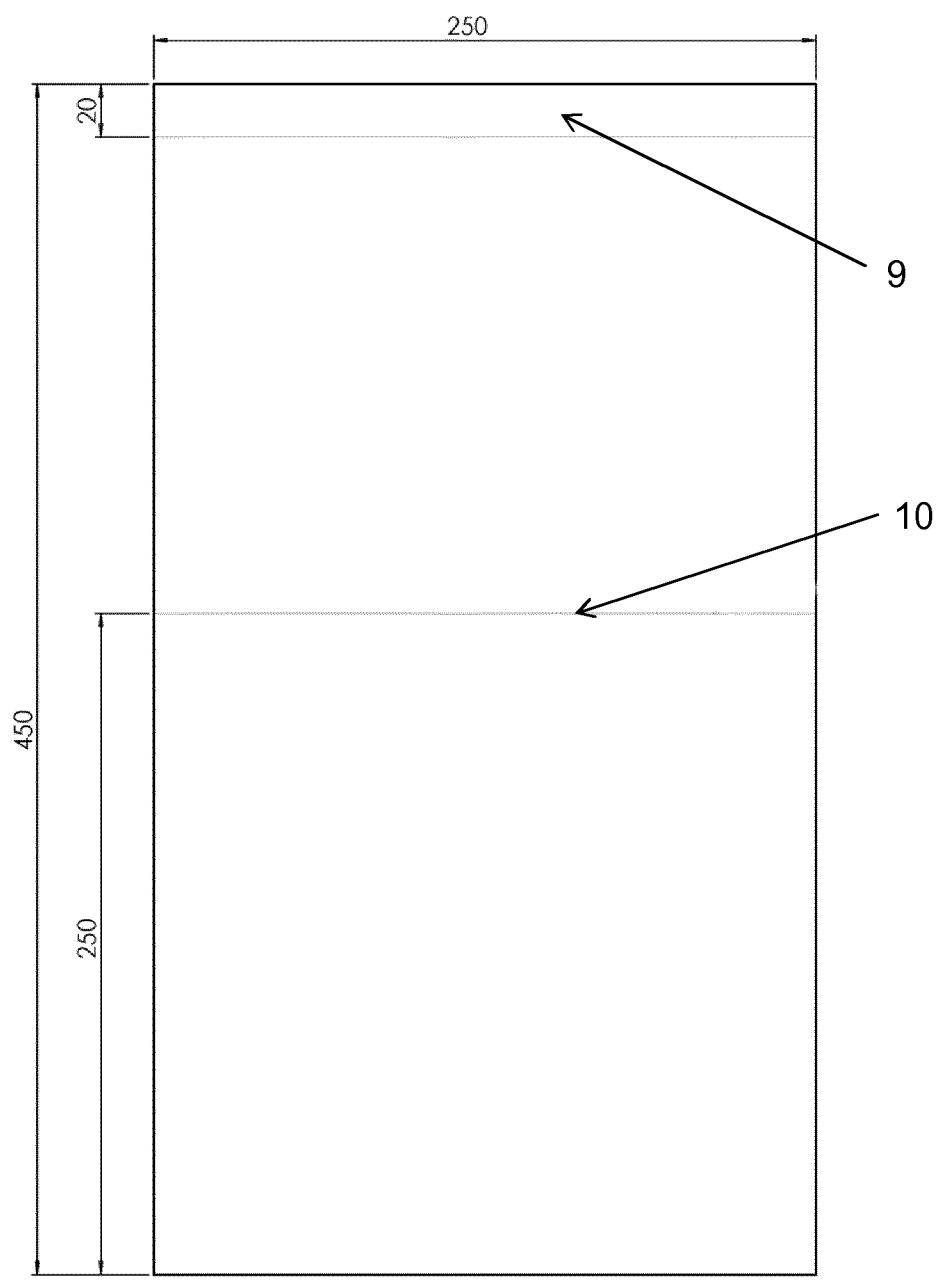
FIG. 9 is a schematic of an embodiment of the second bag for putting the disposable bag containing the waste into after use.

FIG. 9 is a schematic of an embodiment of the second bag for putting the disposable bag containing the waste into after use. This second bag will provide an extra seal for the waste which further reduces the risk of leakage and odor from the bag. In this embodiment the open end of the second bag is provided with a strip of rigid material 9, such as a plastic strip. After the disposable bag with waste is put into the second bag, the strip is folded multiple times to create a seal at the open end of the second bag. Furthermore, the bag may have an adhesive strip 10 for securing the strip of rigid material 9 to after folding the bag around it.

It will be apparent to those skilled in the art that various modifications and variations can be made in the present disclosure without departing from the scope of this disclosure. It is to be understood that the detailed description of the present disclosure are exemplary and explanatory and are intended to provide further explanation of the disclosure. It is not intended to be exhaustive or to limit embodiments to the precise form disclosed.

The invention claimed is:

1. A disposable bag, comprising:
a plastic bag attachable to a toilet, the bag being fabricated from a material adapted for collecting bodily waste, in the form of urine, feces or vomit, which contains toxic materials from chemotherapy treatment;
a hem defining an opening of the bag with an elastic band located inside the hem configured for securing the bag to the toilet during use; and
an absorbent pad inside the bag configured for absorbing liquid from the bodily waste, wherein the absorbent pad contains a superabsorbent polymer or an absorbent gel material for absorbing the liquid in the bodily waste.

2. The disposable bag according to claim 1, further comprising a string inside the hem configured for securely closing and/or sealing the bag after use.

3. The disposable bag according to claim 1, further comprising a second hem at the edge of the bag with a string inside configured for securely closing and/or sealing the bag after use.

4. The disposable bag according to claim 1, further comprising at least one aperture at the hem such that the elastic band can be withdrawn through the aperture and used to securely close and/or seal the bag after use.

5. The disposable bag according to claim 1, wherein the size of the absorbent pad is configured to absorb at least 300 mL of liquid, or at least 500 mL of liquid, or at least 750 mL of liquid.

6. The disposable bag according to claim 1, further comprising a waterproof adhesive configured for attaching the absorbent pad to the bag.

7. The disposable bag according to claim 1, wherein the plastic material for the bag is linear low-density polyethylene, or polyurethane, or a bio-based plastic.

8. The disposable bag according to claim 1, wherein the material for the bag is puncture-resistant and/or tear-resistant.

9. The disposable bag according to claim 8, wherein the puncture-resistance and/or tear-resistance is established through the thickness and/or the elasticity of the material.

10. The disposable bag according to claim 1, configured for being fitted through the toilet seat, folded around the toilet seat and tucked under the toilet seat.

11. The disposable bag according to claim 1, configured to conform to the shape of the toilet in a way such that the bag does not touch the inside of the toilet bowl or the water in the toilet.

12. The disposable bag according to claim 11, configured to conform to the shape of the toilet by tightening the elastic band such that a sufficient amount of the bag is pulled under the toilet seat which prevents the bag from touching the inside of the toilet bowl and/or the water in the toilet.

13. The disposable bag according to claim 1, wherein the bag is fabricated from two hemispherical sheets of plastic material joined at the curved edge and with the opening at the straight edge.

14. The disposable bag according to claim 1, wherein the bag is fabricated from two sheets of plastic material in the shape of a Y or a funnel joined at the bottom and side edges such that it is wide at the opening at the top and narrower at the bottom.

15. The disposable bag according to claim 14, wherein the width of the bag at the bottom is at least 20 percent, or at least 40 percent, or at least 60 percent smaller than the width of the bag at the opening.

16. The disposable bag according to claim 1, wherein the bag is made from double layered plastic.

17. The disposable bag according to claim 1, wherein the thickness of the plastic material for the bag is at least 20 microns, or at least 40 microns, or at least 60 microns, or at least 100 microns, or at least 150 microns.

18. The disposable bag according to claim 1, wherein the diameter of the opening of the bag in a fully stretched configuration is 40-50 cm, or 50-60 cm, or 60-70 cm, or 70-80 cm, or 80-90 cm.

19. The disposable bag according to claim 1, wherein the circumference of the opening of the bag in a stretched configuration is 130-135 cm, 135-140 cm, or 140-145 cm or 145-150 cm.

20. The disposable bag according to claim 1, wherein the distance from the hem of the bag to the bottom of the bag is 20-25 cm, or 25-30 cm, or 30-35 cm, or 35-40 cm, or 40-45 cm.

21. The disposable bag according to claim 1, configured such that upon attachment to a toilet seat the bottom of the bag extends less than 25 cm below the toilet seat, or less than 20 cm below the toilet seat, or less than 15 cm below the toilet seat.

22. A kit comprising the disposable bag according to claim 1 and a second outer bag to put the disposable bag in after use in case the first bag touched the inside of the toilet bowl and/or for creating an extra seal for the waste.

23. The kit according to claim 22, further comprising a set of plastic or rubber gloves.

24. The kit according to claim 22, wherein the second bag is fabricated from linear low-density polyethylene, or polyurethane, or a bio-based plastic.

25. The kit according to claim 22, wherein the thickness of the plastic material for the second plastic bag is at least 20 microns, or at least 40 microns, or at least 60 microns, or at least 100 microns, or at least 150 microns.

26. The disposable bag according to claim 7, wherein the bio-based plastic is selected from the group of Starch-based plastics, cellulose-based plastics, protein-based plastics, aliphatic polyesters, polyamide 11, bio-derived polyethylene, polyhydroxyurethanes and lipid-derived polymers.

27. The disposable bag according to claim 24, wherein the bio-based plastic is selected from the group of Starch-based plastics, cellulose-based plastics, protein-based plastics, aliphatic polyesters, polyamide 11, bio-derived polyethylene, polyhydroxyurethanes and lipid-derived polymers.

* * * * *